United States Patent
Hooft et al.

(10) Patent No.: US 6,411,676 B1
(45) Date of Patent: Jun. 25, 2002

(54) METHOD FOR DETERMINING PARAMETERS OF A UNIT CELL OF A CRYSTAL STRUCTURE USING DIFFRACTION

(75) Inventors: Robertus Wilhelmus Hooft, Gravenzande; Albert Jozef Duisenberg, Utrecht; Antonius Matthias Schreurs, Nieuwerbrug, all of (NL)

(73) Assignee: Nonius B.V., Delft (NL)

( * ) Notice: Subject to any disclaimer, the term of this patent is extended or adjusted under 35 U.S.C. 154(b) by 0 days.

(21) Appl. No.: 09/674,461

(22) PCT Filed: Apr. 1, 1999

(86) PCT No.: PCT/NL99/00197

§ 371 (c)(1),
(2), (4) Date: Dec. 22, 2000

(87) PCT Pub. No.: WO99/56115

PCT Pub. Date: Nov. 4, 1999

(30) Foreign Application Priority Data

Apr. 28, 1998 (NL) .............................................. 1009012

(51) Int. Cl.$^7$ .......................................... G01N 23/207
(52) U.S. Cl. .......................................... 378/73; 378/71
(58) Field of Search ............................. 378/73, 71, 70, 378/79; 250/269.4, 505.1

(56) References Cited

U.S. PATENT DOCUMENTS

| | | | | |
|---|---|---|---|---|
| 3,394,255 A | * | 7/1968 | Furnas, Jr. .................. 250/51.5 |
| 4,412,345 A | * | 10/1983 | Workman et al. ............. 378/78 |
| 4,710,259 A | * | 12/1987 | Howe et al. ................. 156/601 |
| 5,359,640 A | * | 10/1994 | Fink et al. .................... 378/79 |
| 5,878,106 A | * | 3/1999 | Fujiwara ..................... 378/79 |

FOREIGN PATENT DOCUMENTS

| DE | 19945773 A1 | * | 4/2001 | ........... G21K/1/06 |
|---|---|---|---|---|
| JP | 60093335 | | 5/1985 | |
| JP | 8327565 | | 12/1996 | |

\* cited by examiner

Primary Examiner—Robert H. Kim
Assistant Examiner—Irakli Kiknadze
(74) Attorney, Agent, or Firm—Darby & Darby

(57) ABSTRACT

A method for determining the parameters of a unit cell of a crystal structure using diffraction is presented. The method includes the steps of repeatedly rotating the crystal at a predetermined angle, while the crystal moves in relation to a detection surface and measuring the position of radiation reflected from the crystal. The resulting combined measurements are utilized to accurately determine the unit cell dimension and orientation of the crystal.

7 Claims, 2 Drawing Sheets

FIG 1 - prior art

Figure 1:
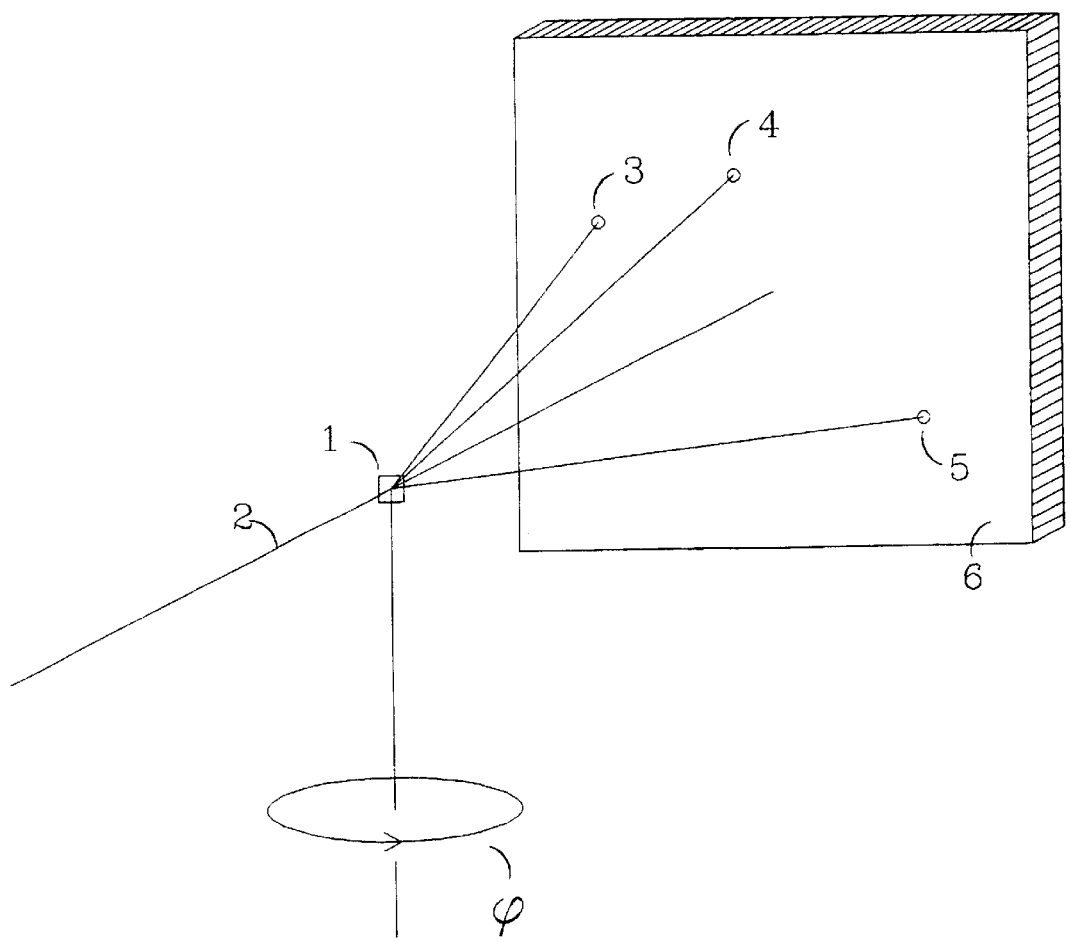

METHOD FOR DETERMINING PARAMETERS OF A UNIT CELL OF A CRYSTAL STRUCTURE USING DIFFRACTION

FIELD OF THE INVENTION

The invention relates to a method of determining parameters of a unit cell of a crystal structure, in particular the dimensions and orientation of a unit cell, using diffraction, comprising the following steps: a. directing X- or neutron rays at a crystal rotating over a predetermined angle; b. detection of the radiation reflected by the crystal on a two-dimensional detection surface; c. determining the position where the reflected radiation falls on the detection surface.

BACKGROUND OF THE INVENTION

Such a method is known from practice. In the known method the reflections of the beams directed at the crystal are detected on a position-sensitive detector, for example, a photo-sensitive plate, and on the basis of these positions which are processed further, the cell parameters of the crystal structure are determined in order to explain the respective reflection positions on the detection surface. According to the prior art the crystal is repeatedly rotated over an angle of, for example, 1 or 2°. As a result, the cell parameter of the crystal structure determined by this prior art technique is cursed with relatively large inaccuracies. The position of the reflections in the two directions of the detector surface is indeed determined accurately; however, the position of the crystal has an uncertainty amounting to several tenths of degrees. The unit cells composing the crystal structure will then exhibit deviations of several hundredth to one tenth degree or even more, with respect to the corners that are distinguishable in the unit cells. This accuracy can be improved by limiting the rotation of the crystal during measuring to approximately 0.1 or 0.2°, however, the number of measurements required then increases correspondingly.

It is the object of the invention to provide a method for determining the parameters of a unit cell of a crystal structure that can be performed quickly and requires little measuring time.

To this end the method of determining parameters of a unit cell of a crystal structure using diffraction according to the invention is characterized in that the steps a, b and c are repeated, wherein in step a the crystal always rotates over the same angle, that in the first performance of the steps a, b and c the relative movement of the crystal in relation to the detection surface is determined by only the rotation of the crystal, that in a repeat-performance of the steps a, b and c the relative movement of the crystal in relation to the detection surface is determined by a rotation of the crystal identical to that of the first performance of the steps a, b and c, and by a further relative movement of the crystal in relation to the detection surface coupled thereto, and that the combination of the positions determined in the repeat performance of steps c determines the angle position of the crystal in relation to a reference value in which reflection of the beams occurs.

The idea of the invention is based on the intelligence that when performing repeat-measurements, the position of the reflections on the detection surface in relation to the previous measurement can only be influenced by the additional relative movement of the crystal in relation to the detection surface. Because the relative movement of the crystal in relation to the detection surface is known and added to the rotation of the crystal which is also known, it is possible by means of generally known techniques to determine the position of the crystal whereby the reflections have occurred. This position of the crystal, together with the position of the reflections on the detection surface, provides sufficient information to derive more accurately than with the prior art, the unit cell parameters that determine the crystal structure. Further details about the determination of the crystal structure may be left aside, as the person skilled in the art will be quite familiar with these.

Various embodiments of the method according to the invention are conceivable. A first embodiment of the method according to the invention is characterized in that in the first performance of the steps a, b and c the crystal rotates over a first predetermined angle, and that in the repeat-performance of the steps a, b and c the crystal rotates over the first predetermined angle and the detection surface is moved.

It is desirable that in the repeat-performance of the steps a, b and c the crystal rotate over a first predetermined angle and the detection surface be rotated over a second predetermined angle. This may conveniently be performed in existing diffraction devices such as marketed, for example, by Nonius B. V. at Delft.

A second embodiment of the method according to the invention is characterized in that in the first performance of the steps a, b and c the crystal rotates over the first predetermined angle, and that in the repeat-performance of the steps a, b and c the crystal rotates over the first predetermined angle while in addition undergoing a movement superposed on this rotation.

It is desirable that the superposed movement of the crystal be a rotation in a plane cutting the rotation plane in which the first predetermined angle lies. This method may also be performed very suitably using existing diffraction devices as marketed by Nonius B. V. at Delft.

The method according to the invention further differs from the prior art in so far that during measurement the first predetermined rotation angle of the crystal is approximately 20° or more. By performing the measurements with such a relatively large angular displacement it is possible to obtain all the necessary information for the determination of the parameter of a unit cell of the crystal structure, even of very small unit cells, with just two successive measurements. By suitably choosing the additional relative movement of the detection surface in relation to the crystal it is moreover possible to render the method according to the invention sufficiently accurate. If in order to obtain this additional relative movement the detection surface is, for instance, rotated, the second predetermined angle may be adjusted to approximately 10°. Such an angle displacement is also useful if the additional movement is carried out by the crystal.

DETAILED DESCRIPTION OF THE INVENTION

Figure 2:
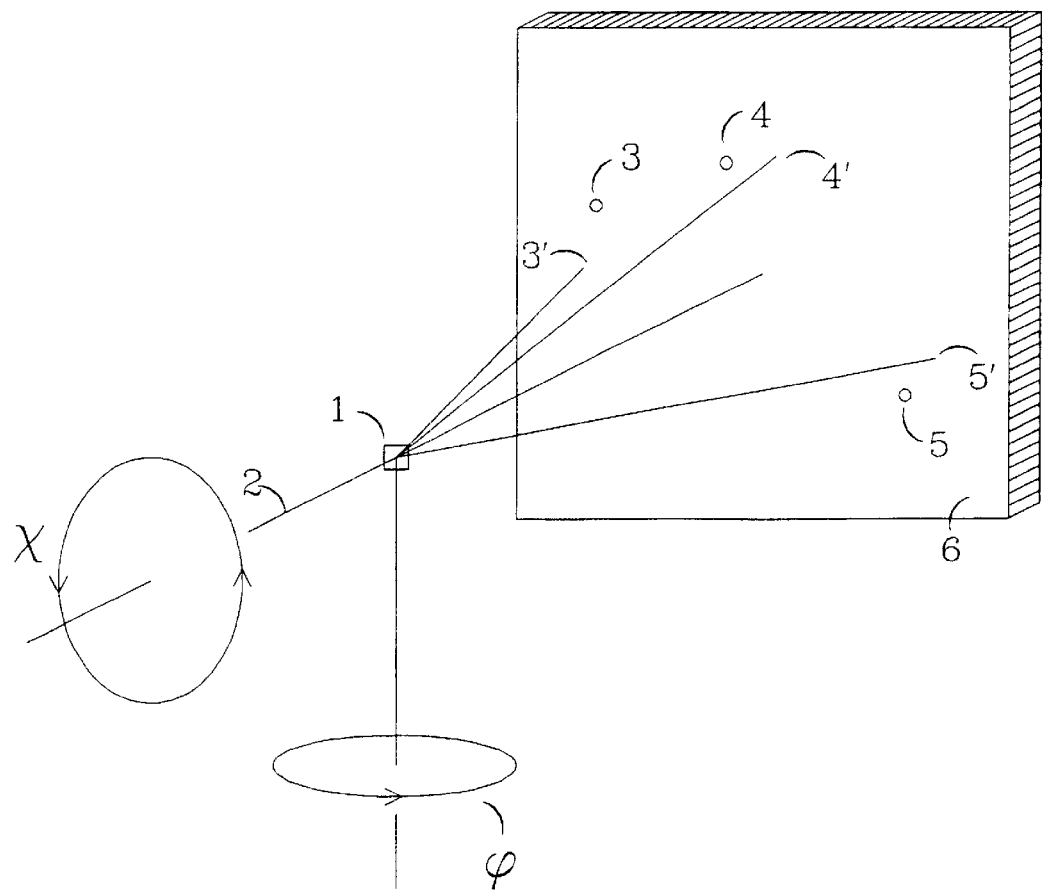

The invention will now be explained in more detail with reference to the drawing, which in FIG. 1 shows schematically the method of determining a crystal structure according to the prior art; and in FIG. 2 shows the method of determining a crystal structure according to the invention in a preferred embodiment.

Those parts in the Figures that are the same are indicated by identical reference numbers.

In the FIGS. 1 and 2 reference number 1 indicates the crystal whose structure and thus the parameters of a unit cell, are to be determined. A beam, for example, an X-ray beam 2, is directed at the crystal while the crystal 1 is simultaneously rotated over a predetermined angle. This is indicated in the FIGS. 1 and 2 by the elliptical rotation symbol carrying reference $\phi$. During the rotation over an angle $\phi$ the X-rays 2 are reflected by the crystal 1, projecting reflection images 3, 4 and 5 on the detection surface 6. Instead of X-ray beams it is also possible to use other suitable beams such as neutron beams. The detection surface 6 may, for example, be a CCD camera that is part of a device for measuring X-ray diffraction. Finally, based on the position of the image points 3, 4 and 5 and others on the detection surface 6, the unit cell parameters of a crystal 1 are determined.

According to the invention, after carrying out the method as explained above with reference to FIG. 1 and whereby the image points 3, 4 and 5 are formed, a repeat-measurement is performed, wherein again X-rays 2 are directed at the crystal 1, and the reflected X-ray beams are detected on the detection surface 6, to determine the image positions then formed on the detection surface 6. During this repeat-performance of the measurement the crystal 1 is rotated over an identical angle $\phi$, but in addition to this movement of the crystal 1 in relation to the detection surface 6, the crystal 1 performs another relative movement in relation to the detection surface 6, which movement in this preferred embodiment is a second rotation of the crystal 1 over an angle $\chi$ (see FIG. 2) in a plane cutting the rotation plane of the crystal in which lies the first predetermined angle $\phi$. From the combination of the positions of image points 3, 4 and 5 determined in the first measurement with the image points 3', 4' and 5' from the repeat-measurement, it is possible to accurately determine the position or positions of the crystal 1 in which the reflections of the X-rays 2 have occurred. These positions of the crystal together with the previously-mentioned position of the image points suffice to accurately determine the unit cell dimensions and the orientation of the crystal.

The above description of an embodiment merely serves to explain the appended claims, without in any way limiting their protective scope.

What is claimed is:

1. A method of determining parameters of a unit cell of a crystal structure using diffraction, comprising the following steps:

a. directing X- or neutron rays at a crystal rotating over a predetermined angle;

b. detection of the radiation reflected by the crystal on a two-dimensional detection surface;

c. determining the position where the reflected radiation falls on the detection surface, characterized in that the steps a, b and c are repeated, wherein in step a the crystal rotates always over the same angle, that in the first performance of the steps a, b and c the relative movement of the crystal in relation to the detection surface is determined by only the rotation of the crystal, that in a repeat-performance of the steps a, b and c the relative movement of the crystal in relation to the detection surface is determined by a rotation of the crystal identical to that of the first performance of the steps a, b and c, and by a further relative movement of the crystal in relation to the detection surface coupled thereto, and that the combination of the positions determined in the repeat performance of steps c determines the angle position of the crystal in relation to a reference value in which reflection of the beams occurs.

2. A method according to claim 1, characterized in that in the first performance of the steps a, b and c the crystal rotates over a first predetermined angle, and that in the repeat-performance of the steps a, b and c the crystal rotates over the first predetermined angle and the detection surface is moved.

3. A method according to claim 2, characterized in that in the repeat-performance of the steps a, b and c the crystal rotates over the first predetermined angle and the detection surface rotates over a second predetermined angle.

4. A method according to claim 1, characterized in that in the first performance of the steps a, b and c the crystal rotates over the first predetermined angle, and that in the repeat-performance of the steps a, b and c the crystal rotates over the first predetermined angle while in addition undergoing a movement superposed on this rotation.

5. A method according to claim 4, characterized in that the superposed uniform movement of the crystal is a rotation in a plane cutting the rotation plane in which the first predetermined angle lies.

6. A method according to claim 1, characterized in that the first predetermined angle of rotation of the crystal is at least approximately 20°.

7. A method according to claim 3, characterized in that the second predetermined angle of rotation of the detection surface of the crystal is approximately 10°.

* * * * *